United States Patent [19]

Reisser

[11] Patent Number: 4,499,280
[45] Date of Patent: Feb. 12, 1985

[54] TRIAZOLES, AND THEIR USE AGAINST INSECT PESTS

[75] Inventor: Fritz Reisser, Therwil, Switzerland

[73] Assignee: Sandoz Ltd., Basel, Switzerland

[21] Appl. No.: 398,670

[22] Filed: Jul. 15, 1982

[30] Foreign Application Priority Data

Jul. 17, 1981 [GB] United Kingdom ............... 8122064

[51] Int. Cl.$^3$ .................... A01N 43/64; C07D 249/06
[52] U.S. Cl. .................................... 548/255; 260/349
[58] Field of Search ......................................... 548/255

[56] References Cited

U.S. PATENT DOCUMENTS 3,579,531 5/1971 Scheiner .............................. 424/269

FOREIGN PATENT DOCUMENTS 0046192 2/1982 European Pat. Off. ............ 548/255

OTHER PUBLICATIONS

Chattaway et al., Chem. Abstracts, vol. 19, pp. 476–477, (1925).
Bayer, Chem. Abstracts, vol. 67, Abstract No. 100995, (1967).
Burger, Medicinal Chemistry, (Second Edition, New York, 1960), p. 1055.
Horsfall, Fungicides and Their Action, (Waltham, Mass., 1945) p. 151.

Primary Examiner—Alton D. Rollins
Attorney, Agent, or Firm—Gerald D. Sharkin; Richard E. Vila

[57] ABSTRACT

The invention provides a method of reducing the feeding activity of insects on plants with the aid of 1,2,3-triazoles being unsubstituted in the 4- and 5-positions and bearing a phenyl moiety in the 1-position, fungicidal compositions comprising such triazoles and novel 1,2,3-triazoles.

1 Claim, No Drawings

TRIAZOLES, AND THEIR USE AGAINST INSECT PESTS

The present invention relates to 1-phenyl-1,2,3-triazoles having anti-feedant properties, a method of inhibiting the feeding activity of insects on plants with the aid of such compounds, to compositions applicable to that method, to a group of novel compounds and to their preparation.

Various 1-phenyl-1,2,3-triazoles are known (see "Triazoles: 1,2,3" by K. Th. Finley and J. A. Montgomery, edited by J. Wiley & Sons, 1980, e.g. on page 10 to 12). It is also known that 1-monohalophenyl-1,2,3,-triazoles have fungicidal and miticidal properties (U.S. Pat. No. 3,579,531). It has now been found that certain 1-phenyl-1,2,3-triazoles can be used to reduce the feeding activity of insects. An objective of this invention is to substantially diminish the damage caused by insects to plants.

Accordingly, the present invention provides a method of reducing the feeding activity of insects on plants which comprises applying to said plants an anti-feedant effective amount of a 1,2,3-triazole being unsubstituted in the 4- and 5-positions and bearing a phenyl moiety in the 1-position (hereinafter 1-phenyl-1,2,3-triazoles of the invention), with the proviso that where said phenyl moiety is monohalophenyl, the insects are of the class Insecta.

By "plants" is meant any vegetable material, including for example wood, stored products of vegetable origin such as grain, seeds etc. Preferred is the use of the method of the invention in crops.

The 1-phenyl moiety of the 1-phenyl-1,2,3-triazoles of the invention suitable for use in the method of the invention may be unsubstituted or substituted by one or more substituents acceptable in the insecticidal field. Suitable substituents of such phenyl moiety are e.g. selected from halogen; CN; $NO_2$; $C_{1-5}$alkyl; $C_{1-5}$alkyl substituted by halogen; $C_{1-5}$alkylthio; $C_{1-5}$alkylsulphinyl; $C_{1-5}$alkylsulphonyl; $C_{1-5}$alkoxy; $C_{1-5}$alkoxy substituted by halogen; phenyl or phenoxy; phenyl or phenoxy substituted by halogen, $C_{1-5}$alkyl, $C_{1-5}$alkoxy and/or $NO_2$; $C_{2-5}$alkanoylamino; benzoylamino; $C_{7-12}$phenylalkyl Any halogen substituent present in the 1-phenyl-1,2,3-triazoles of the inventions is selected from F, Cl and Br.

The term insect as used therein, is used in a wide sense and may include organisms of the class Insecta, as well as related classes of Arthropoda, e.g. Acarina such as Tetranychidae.

1-Phenyl-1,2,3-triazoles particularly suitable for use in the method of the invention are of the formula I

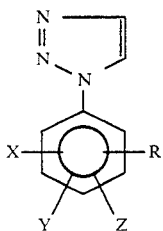

wherein
X is H, halogen selected from F, Cl and Br; CN; $NO_2$; $C_{1-5}$alkyl; $C_{1-5}$alkyl substituted by halogen selected from F, Cl or Br; $C_{1-5}$alkylthio; $C_{1-5}$alkylsulphinyl; $C_{1-5}$alkylsulphonyl; $C_{1-5}$alkoxy; $C_{1-5}$alkoxy substituted by halogen selected from F, Cl or Br; phenyl or phenoxy; phenyl or phenoxy substituted by $C_{1-5}$alkyl, $C_{1-5}$alkoxy, $NO_2$ and/or halogen; $C_{2-5}$alkanoylamino; benzoylamino; $C_{7-12}$phenylalkyl;

Y is H; halogen selected from F, Cl, or Br; $NO_2$; $C_{1-5}$alkyl; $C_{1-5}$alkyl substituted by halogen selected from F, Cl or Br; $C_{1-5}$alkoxy and $C_{1-5}$alkoxy substituted by halogen selected from F, Cl or Br;

Z is H; halogen selected from F, Cl or Br; $C_{1-5}$alkyl; $C_{1-5}$alkoxy;

R is H or halogen selected from F, Cl or Br.

Where any of X, Y, Z or R is or comprises halogen this is preferably F or Cl.

Where any of X, Y or Z is or comprises $C_{1-5}$alkyl, it is e.g. a $C_{1-3}$alkyl group such as $CH_3$.

Where any of X or Y is $C_{1-5}$alkyl or $C_{1-5}$alkoxy substituted by halogen said $C_{1-5}$alkoxy may be mono-, di- or tri-substituted. Examples of such substituents are $CH_2Cl$, $CF_3$, $OCF_3$ etc.

The method of the invention is useful as illustrated by tests showing a reduction of the damage caused by insects to a crop such as cotton infested with Spodoptera larvae, after treatment of the leaves and/or roots with test concentrations of 20 to 2500 ppm. The insects soon stop feeding, which is evident from the comparison of the remaining partially undamaged treated leaf surface with that of an untreated standard after a given time period e.g. 24 hours. The insects that have licked from the treated material will usually die from starvation, even when they are afterwards put on untreated material. The 1-phenyl-1,2,3-triazoles of the invention can consequently be considered as anti-feedants (in contrast to repellants which simply keep the insect from approaching). The 1-phenyl-1,2,3-triazoles of the invention have the particular advantage of being systemic anti-feedant. This systemic action is i.a. indicated by tests where the 1-phenyl-1,2,3-triazoles of the invention execute their anti-feedant activity in leaves of plants (e.g. cotton) of which only the roots are treated.

For the anti-feedant use of the 1-phenyl-1,2,3-triazoles of the invention, the amount to be applied to attain the desired effect will vary depending on the particular insect, the plant if employed for agricultural use and other standard variables such as the compound employed, mode of application, conditions of treatment and the like. The appropriate application rates can be determined by routine procedures by those skilled in the art. For agricultural use, in general, satisfactory results are usually obtained when the 1-phenyl-1,2,3-triazole compound is applied at a rate in the range of from about 50 to 5000 g per/ha, particularly from 100 to 2000 g/ha of crop locus, the application being repeated as necessary.

A preferred embodiment of the invention is the use of the method of the invention in cotton and cruciferous crops such as broccoli, brussels sprouts, cabbage. The anti-feedant activity is particularly effective against insects of the class Insecta, more specifically against chewing insects especially against insects of the order Coleoptera, e.g. against Coleoptera of the family Chrysomelidae such as *Phaedon cochleariae* and against insects of the order Lepidoptera, e.g. against Lepidoptera of the family Yponomeutidae such as *Plutellidae spp* (for example Plutella maculipennis) and against Lepidoptera of the family Noctuidae such as *Spodoptera spp*.

Particularly effective anti-feedant activity is observed when the 1-phenyl moiety is multiple substituted, e.g. disubstituted or tri-substituted.

Where the 1-phenyl moiety is disubstituted, particular suitable substituents are selected from the group consisting of $CF_3$ and halogen, (such as Cl); the substituents are then preferably in the 3- and 4- or the 3- and 5-positions particularly the 3- and 5-positions. Thus, 1-(3,4-dichlorophenyl)-1,2,3-triazole and 1-(3,5-dichlorophenyl)-1,2,3-triazole possess excellent anti-feedant activity.

Where the 1-phenyl moiety is tri-substituted, preferred sub-groups thereof have their substituents in the 2-, 4- and 6-positions thereof and/or are tri-halogenated, particularly trichloro compounds.

The 1-phenyl-1,2,3-triazoles of the invention may be and preferably are employed as anti-feedant compositions in association with agriculturally acceptable diluents. Such anti-feedant compositions also form part of the present invention. Typical formulations include compositions of the active ingredient in combination with an agriculturally acceptable diluent, optionally with an agriculturally acceptable surfactant and optionally with other active ingredients. Pesticidal formulations comprising a compound of formula I are novel, provided that in the formula I X is not halogen when Y, Z and R are hydrogen. Suitable formulations include solid forms, such as granules and powders or liquids. Thus the active ingredients may be formulated as granules of various sizes, as dusts, as wettable powders, as emulsifiable concentrates, as solutions, as dispersions, as controlled release compositions, and the like. Such compositions may be produced in conventional manner, e.g. by mixing the active ingredient with a diluent and optionally other formulating ingredients such as surfactants. A typical formulation may vary widely in concentration of the active ingredient depending upon the particular agent used, the diluent(s) and surfactant(s) used, other active ingredients and the desired mode of application. With due consideration of these factors, the active ingredient of a typical formulation may, for example, be suitably present as a concentration of about 0.01% up to about 95% by weight of the formulation. An agriculturally acceptable diluent may comprise about 99.99% by weight to as low as about 5% by weight of the formulation. Compatible agriculturally acceptable surfactants may be present at various concentrations, suitably in the range of 0% to 30% by weight of the formulation. Surfactants such as wetting and dispersing agents are particularly contained in formulations to be applied in spraying forms such as water dispersible concen-trates or wettable powders. Examples of suitable surfactants are the condensation product of formaldehyde with naphthalene sulphonate, an alkylarylsulphonate, a lignin sulphonate, a fatty alkylsulphate, an ethoxylated alkylphenol and an ethoxylated fatty alcohol.

The formulation may be used as such or diluted to a desired use dilution with an agriculturally acceptable diluent. The concentration of the active ingredient in the use dilution may be in the range of about 0.01% to about 10% by weight. The term diluent as used herein means any liquid or solid agriculturally acceptable material which may be added to the active constituent to bring it in an easier or improved applicable form, respectively to a usable or desirable strength of activity. It can for example be talc, kaolin, diatomaceous earth, xylene, an oil or water.

Many variations of spraying, dusting and controlled or slow-release compositions of a type known in the art may be used by substituting or adding a 1-phenyl-1,2,3-triazole of this invention into the compositions known or apparent to the art.

The compounds of formula Ia

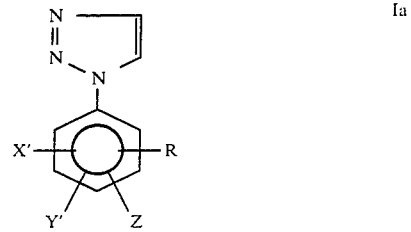

wherein
X' is halogen selected from F, Cl and Br; CN; $C_{1-5}$alkyl; $C_{1-5}$alkyl substituted by halogen selected from F, Cl or Br; $C_{1-5}$alkylthio; $C_{1-5}$alkylsulphinyl; $C_{1-5}$alkylsulphonyl; $C_{1-5}$alkoxy; $C_{1-5}$alkoxy substituted by halogen selected from F, Cl or Br; phenyl or phenoxy; phenyl or phenoxy substituted by $C_{1-5}$alkyl, $C_{1-5}$alkoxy, $NO_2$ and/or halogen selected from F, Cl or Br; $C_{3-5}$alkanoylamino; benzoylamino; $C_{7-12}$phenylalkyl;
Y' is halogen selected from F, Cl or Br; $C_{1-5}$alkyl; $C_{1-5}$alkyl substituted by halogen selected from F, Cl or Br; $C_{1-5}$alkoxy or $C_{1-5}$alkoxy substituted by halogen selected from F, Cl or Br, and
Z and R are as defined above,
with the proviso that where X' and Y' are both halogen, they are only in the 2,4- or 2,5-positions when at least one of Z and R is different from H,
are novel and also form part of the invention.

Preferred compounds of formula Ia have one or more of the following features
(a) X' is selected from halogen (particularly chlorine) or haloalkyl (particularly $CF_3$),
(b) Y' is selected from halogen (particularly chlorine) or haloalkyl (particularly $CF_3$),
(c) Z is hydrogen,
(d) R is hydrogen or chlorine,
(e) X' and Y' are in 2,4- or in 3,4- or in 3,5-position.

The invention also provides a process for the production of compounds of formula Ia which comprises reacting a phenyl azide of the formula II

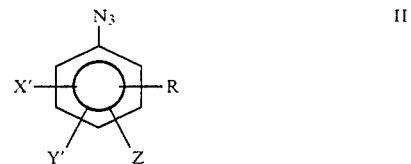

wherein X', Y', Z and R are as defined above, with a vinyl ester of a $C_{1-4}$alkanoic acid.

The above process may be carried out in conventional manner under conditions known for the preparation of 1-phenyl-1,2,3-triazoles, e.g. as described in the U.S. Pat. No. 3,579,531.

The vinyl ester may be used both as reactant and as solvent, and is then used in excess. Preferably the vinyl ester is used as vinyl acetate. The reaction is conveniently carried out at reflux temperature, generally between about 50° C. and about 150° C.

The compounds of formula Ia may be recovered from the reaction mixture in which it is formed by working up according to established procedures.

Insofar as the production of any starting material is not particularly described, these compounds are known or may be produced and purified in accordance with known processes or in a manner analogous to known processes.

Specific examples of anti-feedant compositions will now be described.

EXAMPLE A

Wettable Powder

25 Parts of a compound of formula I, e.g. 1-(3,5-di-trifluoromethylphenyl)1,2,3-triazole, 5 parts of a condensation product from formaldehyde and naphthalene sulphonate, 2 parts of an alkyl benzene sulphonate, 5 parts dextrin, 1 part of ammonium caseinate and 62 parts of diatomaceous earth are mixed until a homogeneous mixture is obtained and then ground until the particles are considerably smaller than 45 microns as an average.

EXAMPLE B

Emulsion Concentrate

25 Parts of a compound of formula I, e.g. 1-(3,5-di-trifluoromethylphenyl)-1,2,3-triazole, 65 parts of xylene, 10 parts of a mixture of the reaction product of an alkyl-phenol with ethylene oxide and calcium-dodecyl benzene sulphonate are until a homogeneous solution is obtained. The resulting emulsion concentrate is diluted with water before use.

EXAMPLE C

Granulate

5 Kg of a compound of formula I, e.g. 1-(3,5-di-trifluoromethylphenyl)-1,2,3-triazole are dissolved in 25 liters methylene chloride. The solution is then added to 95 kg of granulated attapulgite (24/48 mesh/inch) and thoroughly mixed. The solvent is then evaporated off under reduced pressure with warming.

The following Examples, in which all parts and percentages are by weight and temperatures are in °C., further illustrate the invention.

EXAMPLE 1

1-(3,5-Di-trifluoromethylphenyl)-1,2,3-triazole

A sulphonation flask (350 ml) is charged with 18.8 g 3,5-di-trifluoromethylphenylazide and 120 ml vinyl acetate, the reaction mixture refluxed (at 71°–73°; at atmospheric pressure) during 24 hours, concentrated and the precipitated crystalline product recrystallized from methanol to give the pure title compound m.p. 102°–103°.

EXAMPLE II

Following the procedure of Example 1, but employing appropriate compounds of formula II, the following compounds of formula I are obtained:

| Example | X | Y | Z | R | Characterization (m.p.) |
|---|---|---|---|---|---|
| A | 3-Cl | 5-Cl | H | H | 132–133° |
| B | 3-Cl | 4-Cl | " | " | 113–114° |
| C | 2-Cl | 5-Cl | " | " | 81–83° |
| D | 2-$CH_3$ | 5-Cl | " | " | Rf*0.35 (diethyl-ether) |
| E | 2-$CH_3$ | 3-Cl | " | " | Rf*0.28 (diethyl-ether) |
| F | 3-$CH_3$ | 5-$CH_3$ | " | " | Rf*0.31 (diethyl-ether) |
| G | 2-Cl | 3-Cl | 4-Cl | 5-Cl | |
| H | 2-F | 3-F | 5-F | 6-F | |
| I | 2-Cl | H | H | H | Rf*0.3 (diethyl-ether) |
| J | 3-Cl | H | " | " | 96–98° |
| K | 4-Cl | H | " | " | 117–118° |
| L | 2-Br | H | " | " | Rf*0.23 ($CH_2Cl_2/CH_3CH$ 98:2) |
| M | 3-Br | H | " | " | 108–109° |
| N | 4-Br | H | " | " | 148–150° |
| O | 2-F | H | " | " | Rf*0.38 (diethyl-ether) |
| P | 3-F | H | " | " | 68–70° |
| Q | 4-F | H | " | " | 78–79° |
| R | 2-Cl | 5-$CF_3$ | " | " | 42–43° |
| S | 2-Cl | 3-Cl | 5-Cl | 6-Cl | 169–171° |
| T | 4-$CH_3CONH$ | H | H | H | 209–210° |
| U | 2-CN | H | " | " | 104–105° |
| V | 3-CN | H | " | " | 135–136° |
| W | 4-CN | H | " | " | 148–150° |
| X | 4-$C_6H_5$ | H | " | " | |
| Y | 2-$C_6H_5CH_2$ | H | " | " | |
| Z | 4-$nC_4H_9O$ | H | " | " | 78–79° |
| $Z_1$ | 4-$C_6H_5O$ | H | " | " | 58–60° |
| $Z_2$ | 2-$CH_3$ | 6-$CH_3$ | " | " | |
| $Z_3$ | 2-Cl | 4-$NO_2$ | 6-Cl | H | |
| $Z_4$ | 4-tert.$C_4H_9$ | H | H | H | |
| $Z_5$ | 3-$CH_3O$ | 5-$CH_3O$ | H | H | 88–90° |
| $Z_6$ | 4-$NO_2$ | H | H | H | |
| $Z_7$ | 3-$NO_2$ | 5-$NO_2$ | H | H | |
| $Z_8$ | 2-Cl | 4-Cl | 5-Cl | H | 108–110° |
| $Z_9$ | 2-Cl | 4-Cl | 6-Cl | H | 178–180° |
| $Z_{10}$ | 3-$CF_3$ | H | H | H | 67–69° |
| $Z_{11}$ | 4-$CH_3CO$ | H | H | H | 175–177° |
| $Z_{12}$ | 4-$C_6H_5CO$ | H | H | H | 168–170° |
| $Z_{13}$ | 4-$nC_4H_9$ | H | H | H | 60–62° |
| $Z_{14}$ | 3-$CF_3$ | 4-Cl | H | H | 78–80° |
| $Z_{15}$ | 2-$CH_3O$ | 4-$CH_3O$ | H | H | 72–74° |
| $Z_{16}$ | 2-$CH_3O$ | 5-$CH_3O$ | H | H | 75–76° |
| $Z_{17}$ | 2-$C_2H_5O$ | 5-$C_2H_5O$ | H | H | 90–92° |
| $Z_{18}$ | 3-$CH_3CO$ | H | H | H | 72–74° |
| $Z_{19}$ | 2-Br | 4-F | H | H | 76–78° |
| $Z_{20}$ | 2-$C_6H_5SO_2$ | H | H | H | Rf*0.25 ($CH_2Cl_2/CH_3OH$ 98:2) |
| $Z_{21}$ | 2-Br | 4-$iC_3H_7$ | H | H | Rf*0.35 (diethyl-ether) |
| $Z_{22}$ | 2-$CF_3$ | 4-Br | H | H | 68–70° |
| $Z_{23}$ | 4-(p-Cl—$C_6H_4O$) | H | H | H | 128–130° |
| $Z_{24}$ | 3-Cl | 4-F | H | H | 114–115° |
| $Z_{25}$ | 4-$CH_3SO_2$ | H | H | H | 194–195° |
| $Z_{26}$ | 4-$CF_3$ | H | H | H | 127–129° |
| $Z_{27}$ | 4-$CH_3O$ | H | H | H | 82–84° |
| $Z_{28}$ | 2-Br | 4-Br | 6-Br | H | 218–220° |
| $Z_{29}$ | 2-Br | 5-Br | H | H | 127–129° |
| $Z_{30}$ | 2-Br | 6-Br | H | H | 141–143° |

*on silica gel

ANTI-FEEDANT TRIALS

TEST 1: *Spodoptera littoralis*/Tradescantia

Plants of Tradescantia are treated until the run off, with solutions containing 2500, 500, 100 and 20 ppm of a compound according to any of examples 1 or 2. After the deposit has become dry, single leaves are placed together with one larva (8 mm long) of *Spodoptera littoralis* in small cups (50 mm wide 30 mm high), covered with a polystyrene cover. 24 Cups per dosage are used. Anti-feedant action of the treatment is determined by measuring the surface area of each leaf with an electronic areameter before and after 24 hours of exposure to the larva.

The compound of Example 1 exhibits a significant anti-feedant activity as indicated by Table I.

TABLE 1

| ppm | (a)* | (b)* |
|---|---|---|
| 2500 | 1.8 | 95.5 |
| 500 | 1.3 | 96.8 |
| 100 | 2.6 | 93.7 |
| 20 | 2.3 | 94.4 |
| untreated | 41.1 | 0 |

*(a) the amount eaten (in cm²) by 24 larvae
(b) % reduction of leaf consumption; (untreated leaves = 0% reduction)

The compounds of Example 2 exhibit a similar degree of anti-feedant activity.

TEST 2: *Spodoptera littoralis*/Cotton

Cotton plants are treated until the run off with solutions containing 500, 100, 20 ppm of a compound of any of the Examples 1 or 2. After the deposit has become dry, single leaves are placed in a polystyrene cup (75 mm wide, 50 mm high), covered with a metal grid. Through a hole in the bottom of the cup, plugged with cotton wool, the petiole of the leaf reaches a water supply. 10 Larvae (8 mm long) of *Spodoptera littoralis* (laboratory strain) are placed in each cup; 4 cups are used per dosage.

The anti-feedant activity is determined after 48 hours exposure to the larvae and expressed as indicated in Test 1. The compound of Example 1 exhibits a significant anti-feedant activity as indicated by Table II.

TABLE II

| ppm | (a)* | (b)* |
|---|---|---|
| 500 | 6.4 | 91.7 |
| 100 | 10.8 | 86.1 |
| 20 | 16.3 | 79.1 |
| untreated | 77.7 | 0 |

*as defined in Test 1.

The compounds of Example 2 exhibit an analogous anti-feedant activity.

TEST 3: *Plutella maculipennis*/China cabbage

One proceeds analogously to Test 2, whereby china cabbage (Brassica chinensis) is used instead of cotton and the tested insect is *Plutella maculipennis* (8 mm long) instead of Spodoptera.

The following anti-feedant activity is observed with the compound of Example 1.

TABLE III

| ppm | (a)* | (b)* |
|---|---|---|
| 500 | 2.9 | 94.7 |
| Untreated | 54.9 | 0 |

*as defined in Test 1.

An analogous anti-feedant activity is obtained with compounds of Example 2.

TEST 4: *Phaedon cochlecriae*/china cabbage

One proceeds as indicated in Test 2, employing however, china cabbage (Brassica chinensis) as test plant and *Phaedon cochlecriae* (adults) as test insect. In each cup is placed one treated and one untreated leaf.

The results obtained with Example 1 are as follows:

TABLE IV

| | Surface leaves eaten (cm²) | | |
|---|---|---|---|
| | After exposure | | |
| ppm | untreated | treated | (b)* |
| 500 | 20.1 | 4.5 | 78 |
| 100 | 16.7 | 2.7 | 84 |
| 20 | 33.1 | 7.1 | 79 |
| 4 | 18.7 | 12.3 | 34 |

*as defined in Test 1.

An analogous anti-feedant activity is found with compounds of Example 2.

TEST 5: *Spodoptera Littoralis*/cotton

Systemic action, Root up-take

Potted cotton plants (20 cm high) are treated by drenching the soil with the test solutions (50 ml per plant). Concentrations used are: 500, 100, 20, 4 ppm of a compound of Examples 1 or 2.

3, 5 10 and 19 Days after application leaves are cut from the plants and submitted to a test as described in Test 2.

The results obtained with the compound of Example 1 are as follows:

TABLE V

| Days after application | 3 | | 5 | | 10 | | 19 | |
|---|---|---|---|---|---|---|---|---|
| ppm | (a)* | (b)* | (a)* | (b)* | (a)* | (b)* | (a)* | (b)* |
| 500 | 6.2 | 92.5 | 7.2 | 92.7 | 15.0 | 77.7 | 33.2 | 76.9 |
| 100 | 11.6 | 85.8 | 2.9 | 97.0 | 40.6 | 39.6 | 71.5 | 50.2 |
| 20 | 24.2 | 70.3 | 35.6 | 63.8 | 40.6 | 39.6 | 96.2 | 33.0 |
| 4 | 29.6 | 63.7 | 49.9 | 49.2 | 49.0 | 27.2 | 117.3 | 18.4 |

*as defined in Test 1.

An analogous anti-feedant activity is found with compounds of Example 2.

TEST 6: *Spodoptera littoralis*/cotton

Persistency trial

Cotton plants (approx. 20 cm high) are treated until the run off with the test solutions containing 1000 and 200 ppm of a compound of Example 1 or 2.

22 Days after treatment treated leaves are cut from the plants and submitted to a test as described in Test 2.

The results obtained with the compound of Example 1 are as follows:

TABLE VI

| ppm | (a)* | (b)* |
|---|---|---|
| 1000 | 14.4 | 73.6 |
| 200 | 29.2 | 46.7 |

*as defined in Test 1.

An analogous anti-feedant activity is found with compounds of Example 2.

TEST 7

One proceeds analogously to Test 2. 3 Hours after treatment of the plant, the leaves are cut and put on moist filter paper in a polystyrene petridish. The larvae (or adults) are then placed on the leaves and after a certain exposure time (e.g. 2, 3 or 5 days), the eaten leaf surface is determined, compared in that of an untreated standard equally exposed to the larvae, and the anti-feedant activity expressed in % reduction of leaf consumption (untreated standard=0%) (see Table VII).

TEST 8: Field Test

Plots of cotton plants are treated with a 1-phenyl-1,2,3-triazole of the invention, e.g. with the compound of Example 1 (formulated according to Example A) at a rate of 0.6 kg of the active ingredient in 1200 liters of water/ha. At various stages after application some leaves of the treated cotton plants are cut and exposed, in the laboratory, to larvae of *Spodoptera littoralis*, according to the method of Test 7.

With the compound of Example 1, a significant reduction of the eaten leaf surface (compared to a untreated standard) is observed, even 21 days after application.

An analogous anti-feedant activity is observed with the compounds of Example 2, such as the compounds of Example 2A, 2B and 2Z$_9$.

TEST 9: Field Test

A cotton culture infested with eggclusters of *Spodoptera littoralis* is sprayed with a 1-phenyl-1,2,3-triazole of the invention at a rate of 1 kg active ingredient in 1000 liters of water per hectare. The treatment is effected as soon as the larvae begin to hatch from the eggs. The degree of protection is established by comparison with an untreated standard. The tested compounds, i.a. the compounds of Examples 1, 2A, 2B and 2Z$_9$ reduce significantly the plant damage.

TABLE VII

| Anti-Feedant Activity | | | | | | | | | | |
|---|---|---|---|---|---|---|---|---|---|---|
| Insect | Spod la (x) | | Trich la (y) | | Plut la (z) | | Phaed la (xy) | | Phaed ad (xz) | |
| Crop | Cotton | | cotton | | China cab. | | China cab. | | China cab. | |
| Days after exposure | 2 | 5 | 2 | 5 | 2 | 3 | 2 | 3 | 2 | 3 |
| Concentration* | | | | | | | | | | |
| Example 2A | | | | | | | | | | |
| 1 | 73 | 86 | 82 | 90 | 66 | 62 | 83 | 83 | 85 | 88 |
| 2 | 69 | 74 | 82 | 87 | 66 | 56 | 86 | 79 | 87 | 86 |
| 3 | 60 | 51 | 78 | 85 | 28 | 28 | 77 | 76 | 77 | 78 |
| 4 | 61 | 43 | 76 | 74 | 28 | 25 | 63 | 62 | 68 | 72 |
| Example 2Z-9 | | | | | | | | | | |
| 1 | 83 | 94 | 89 | 95 | 74 | 76 | 86 | 86 | 85 | 86 |
| 2 | 83 | 93 | 87 | 94 | 77 | 76 | 80 | 83 | 82 | 83 |
| 3 | 63 | 79 | 88 | 95 | 74 | 76 | 66 | 60 | 45 | 45 |
| 4 | 83 | 73 | 83 | 92 | 62 | 66 | 63 | 52 | 39 | 37 |

(x) = Spodoptera larvae;
(y) = Trichoplusia larvae;
(z) = Plutella larvae;
(xy) = Phaedon larvae;
(xz) = Phaedon adults
*Concentration used:

| | 1 | 2 | 3 | 4 |
|---|---|---|---|---|
| Spodoptera | 500 | 250 | 125 | 62.5 ppm active ingredient |
| other insects | 2000 | 1000 | 500 | 250 ppm active ingredient |

What we claim is:
1. The compound 1-(3,5-Di-trifluoromethyl-phenyl)1,2,3-triazole.

* * * * *